(12) United States Patent
Blom et al.

(10) Patent No.: US 8,707,956 B2
(45) Date of Patent: Apr. 29, 2014

(54) ENDOTRACHEAL TUBE HAVING OUTER AND INNER CANNULAE (71) Applicant: Hansa Medical Products, Inc., Carmel, IN (US)

(72) Inventors: Eric D. Blom, Carmel, IN (US); Bradley H. Quinn, Indianapolis, IN (US)

(73) Assignee: Hansa Medical Products, Inc., Carmel, IN (US)

( * ) Notice: Subject to any disclaimer, the term of this patent is extended or adjusted under 35 U.S.C. 154(b) by 0 days.

(21) Appl. No.: 13/691,924

(22) Filed: Dec. 3, 2012

(65) Prior Publication Data

US 2013/0098358 A1 Apr. 25, 2013

Related U.S. Application Data

(60) Continuation-in-part of application No. 12/885,644, filed on Sep. 20, 2010, which is a division of application No. 11/318,649, filed on Dec. 27, 2005, now Pat. No. 7,987,851.

(51) Int. Cl.
*A61M 16/00* (2006.01)
*A62B 9/06* (2006.01)
*A62B 18/08* (2006.01)

(52) U.S. Cl.
USPC ............. 128/207.15; 128/207.14; 128/206.29

(58) Field of Classification Search
CPC ..... A61M 16/00; A61M 16/06; A61M 16/04; A61M 16/0434; A61M 16/044; A61M 16/0461; A61M 16/0463; A61M 16/0465; A61M 16/0468; A61M 16/0472; A61M 16/0683; A61M 2016/04; A61M 2016/0402; A61M 2016/0427; A61M 2016/0475; A61M 2016/0477; A61M 2016/0479; A61M 2016/0484; A61M 2016/0486; A61M 2016/06; A61M 13/00; A61M 13/003; A61M 1/008; A61M 1/0084; A61M 1/0058; A61M 1/0064; A61B 17/24; A61B 17/12022; A61B 9/00; A61B 9/06
USPC ............. 128/204.18, 206.21, 206.29, 207.11, 128/207.14, 207.15, 207.18, 207.29; 606/1, 606/106, 108, 190–198; 604/23, 26, 35
See application file for complete search history.

(56) References Cited

U.S. PATENT DOCUMENTS 1,598,283 A    8/1926   Kinney
2,892,458 A    6/1959   Auzin (Continued)

FOREIGN PATENT DOCUMENTS

DE    37 20 482 A1    12/1988
DE    38 13 705 A1    1/1989

(Continued)

OTHER PUBLICATIONS

Quick Reference Guide to Shiley's "Quality-Of Life" Line of Tracheostomy Products, 1991.

(Continued)

*Primary Examiner* — Rachel Young
(74) *Attorney, Agent, or Firm* — Barnes & Thornburg LLP (57) ABSTRACT

A tracheal tube apparatus includes a cannula having first and second ends. An inflatable cuff is formed on the cannula between the first and second ends. A conduit extends from the cuff for introducing an inflating fluid into the cuff when it is desired to inflate the cuff and removing inflating fluid from the cuff when it is desired to deflate the cuff. A gauge for indicating the inflation pressure of the cuff is coupled in the conduit.

17 Claims, 11 Drawing Sheets

(56) References Cited

U.S. PATENT DOCUMENTS

| | | |
|---|---|---|
| 3,688,774 A | 9/1972 | Akiyama |
| 3,996,939 A | 12/1976 | Sheridan et al. |
| 4,211,234 A | 7/1980 | Fisher |
| 4,223,411 A | 9/1980 | Schoendorfer et al. |
| 4,280,492 A | 7/1981 | Latham |
| 4,304,228 A | 12/1981 | Depel |
| 4,305,392 A | 12/1981 | Chester |
| 4,315,505 A | 2/1982 | Crandall et al. |
| 4,327,721 A | 5/1982 | Goldin et al. |
| 4,449,523 A | 5/1984 | Szachowicz et al. |
| 4,459,984 A | 7/1984 | Liegner |
| 4,469,100 A | 9/1984 | Hardwick |
| 4,573,460 A | 3/1986 | Szachowicz et al. |
| 4,584,998 A | 4/1986 | McGrail |
| 4,589,410 A | 5/1986 | Miller |
| 4,596,248 A | 6/1986 | Lieberman |
| 4,607,635 A | 8/1986 | Heyden |
| 4,617,015 A | 10/1986 | Foltz |
| 4,627,433 A | 12/1986 | Lieberman |
| 4,632,108 A | 12/1986 | Geil |
| 4,637,389 A | 1/1987 | Heyden |
| 4,762,125 A | 8/1988 | Leiman et al. |
| 4,834,087 A | 5/1989 | Coleman et al. |
| 4,840,173 A | 6/1989 | Porter, III |
| 4,852,565 A | 8/1989 | Eisele |
| 5,056,515 A | 10/1991 | Abel |
| 5,067,497 A | 11/1991 | Greear et al. |
| 5,107,828 A | 4/1992 | Koss et al. |
| 5,123,922 A | 6/1992 | Berg |
| 5,201,310 A | 4/1993 | Turnbull |
| 5,217,008 A | 6/1993 | Lindholm |
| 5,218,970 A | 6/1993 | Turnbull et al. |
| 5,255,676 A | 10/1993 | Russo |
| 5,297,546 A | 3/1994 | Spofford et al. |
| 5,329,921 A | 7/1994 | Socaris et al. |
| 5,339,808 A | 8/1994 | Don Michael |
| 5,343,857 A | 9/1994 | Schneider et al. |
| 5,349,950 A | 9/1994 | Ulrich et al. |
| 5,391,205 A | 2/1995 | Knight |
| 5,392,775 A | 2/1995 | Adkins, Jr. et al. |
| 5,458,139 A | 10/1995 | Pearl |
| 5,497,768 A | 3/1996 | Lomholt |
| 5,507,279 A | 4/1996 | Fortune et al. |
| 5,515,844 A | 5/1996 | Christopher |
| 5,584,288 A | 12/1996 | Baldwin |
| 5,599,333 A | 2/1997 | Atkinson |
| RE35,595 E | 8/1997 | Six |
| 5,687,767 A | 11/1997 | Bowers |
| 5,688,256 A | 11/1997 | Surratt et al. |
| 5,746,199 A | 5/1998 | Bayron et al. |
| 5,771,888 A | 6/1998 | Keim |
| 5,957,978 A | 9/1999 | Blom |
| 6,053,167 A | 4/2000 | Waldeck |
| 6,089,225 A | 7/2000 | Brown et al. |
| 6,102,038 A | 8/2000 | DeVries |
| 6,105,577 A | 8/2000 | Varner |
| 6,135,110 A | 10/2000 | Roy |
| 6,135,111 A | 10/2000 | Mongeon |
| 6,254,591 B1* | 7/2001 | Roberson .................. 604/541 |
| 6,463,927 B1 | 10/2002 | Pagan |
| 6,722,367 B1 | 4/2004 | Blom |
| 6,814,077 B1 | 11/2004 | Eistert |
| 7,404,329 B2 | 7/2008 | Quinn et al. |
| 2003/0084905 A1 | 5/2003 | Ortiz |
| 2004/0123868 A1 | 7/2004 | Rutter |
| 2005/0205097 A1* | 9/2005 | Kyle .................... 128/207.14 |
| 2008/0257353 A1* | 10/2008 | Yamamoto et al. ...... 128/205.27 |
| 2011/0011406 A1 | 1/2011 | Blom et al. |
| 2012/0247473 A1* | 10/2012 | Fendler .................. 128/205.27 |

FOREIGN PATENT DOCUMENTS

| | | |
|---|---|---|
| DE | 195 13 831 C1 | 5/1996 |
| DE | 101 09 935 | 11/2001 |
| WO | WO 99/07428 | 2/1999 |
| WO | WO 99/12599 | 3/1999 |
| WO | WO 00/32262 | 6/2000 |

OTHER PUBLICATIONS

Granuloma Associated with Fenestrated Tracheostomy Tubes, Padmanabhan Siddharth, MD, PhD, FACS and Lawrence Mazzarella, MD, FACS, Case Reports, vol. 150, Aug. 1985, pp. 279-280.

D. Hessler, MD, K. Rehder, MD and S.W. Karveth, MD, "Tracheostomy Cannula for Speaking During Artificial Respiration", Anesthesiology, vol. 25, No. 5, pp. 719-721 (1964).

European Search Report from EP 06 02 0526 dated Apr. 19, 2007.

International Search Report from related PCT/US2013/072237 dated Feb. 7, 2014, 8 pages.

* cited by examiner

ENDOTRACHEAL TUBE HAVING OUTER AND INNER CANNULAE

CROSS-REFERENCE TO RELATED APPLICATIONS

This application is a continuation-in-part of U.S. Ser. No. 12/885,644 filed Sep. 20, 2010. U.S. Ser. No. 12/885,644 is itself a divisional of U.S. Ser. No. 11/318,649 filed Dec. 27, 2005, now U.S. Pat. No. 7,987,851. The disclosures of both U.S. Pat. No. 7,987,851 and U.S. Ser. No. 12/885,644 are incorporated herein by reference.

FIELD OF THE INVENTION

This invention relates to improvements in endotracheal tubes, for example, orotracheal tubes and nasotracheal tubes.

BACKGROUND OF THE INVENTION

This invention is directed toward the problem of pooling of saliva and other secretions around the inflated cuff of a tracheal tube, for example, an endotracheal tube, and the potential for such secretions to leak past the cuff and into the lungs. The following are of interest: U.S. Pat. Nos. 1,598,283; 2,892,458; 3,688,774; 3,996,939; 4,211,234; 4,223,411; 4,280,492; 4,304,228; 4,305,392; 4,315,505; 4,327,721; 4,449,523; 4,459,984; 4,469,100; 4,573,460; 4,584,998; 4,589,410; 4,596,248; 4,607,635; 4,627,433; 4,632,108; 4,637,389; 4,762,125; 4,834,087; 4,840,173; 4,852,565; 5,056,515; 5,067,497; 5,107,828; 5,123,922; 5,201,310; 5,217,008; 5,218,970; 5,255,676; 5,297,546; 5,329,921; 5,339,808; 5,343,857; 5,349,950; 5,391,205; 5,392,775; 5,458,139; 5,497,768; 5,507,279; 5,515,844; 5,584,288; 5,599,333; RE35,595; 5,687,767; 5,688,256; 5,746,199; 5,771,888; 5,957,978; 6,053,167; 6,089,225; 6,102,038; 6,105,577; 6,135,110; 6,135,111; 6,463,927; 6,722,367; 6,814,007; 7,404,329; U.S. patent publications: 2003/0084905; 2004/0123868; foreign/international patent publications: DE 25 05 123; DE 34 06 294; DE 37 20 482; DE 38 13 705; DE 195 13 831; DE 101 09 935; WO 99/07428; WO 99/12599; WO 00/32262; other publications: Quick Reference Guide to Shiley's "Quality-Of Life" Line of Tracheostomy Products, 1991; Granuloma Associated with Fenestrated Tracheostomy Tubes, Padmanabhan Siddharth, MD, PhD, FACS and Lawrence Mazzarella, MD, FACS, Case Reports, vol. 150, August 1985, pp. 279-280; Technical Support Information Connections with the Passy-Muir Tracheostomy and Ventilator Speaking Valves, one sheet; Tracheostomy and Laryngectomy Tubes, pp. 568 and 572; Tracheostomy Tube Adult Home Care Guide, Shiley Tracheostomy Products, Mallinckrodt Medical pp. 1-40; D. Hessler, MD, K. Rehder, MD and S. W. Karveth, MD, "Tracheostomy Cannula for Speaking During Artificial Respiration", Anesthesiology, vol. 25, No. 5, pp. 719-721 (1964). No representation is intended by this listing that a thorough search of all material prior art has been conducted, or that no better art than that listed is available. Nor should any such representation be inferred. The disclosures of all of the above are hereby incorporated herein by reference.

SUMMARY OF THE INVENTION

According to an aspect, an endotracheal tube apparatus includes an outer cannula having first and second ends. A fenestration is provided along the length of the outer cannula between the first and second ends. An inflatable cuff is formed on the outer cannula between the fenestration and the second end. A first conduit extends from the cuff for introducing an inflating fluid into the cuff when it is desired to inflate the cuff and removing inflating fluid from the cuff when it is desired to deflate the cuff. An inner cannula is sized selectively to be inserted into, and removed from, the outer cannula. The inner cannula includes a second conduit to evacuate a region of a trachea of a wearer adjacent the cuff. The second conduit includes an opening which lies adjacent the closest point in the fenestration to the cuff when the inner cannula is selectively inserted into a use orientation in the outer cannula.

Illustratively, the apparatus further includes a gauge coupled in the first conduit for indicating the inflation pressure of the cuff.

Illustratively, the apparatus further includes a one-way valve at an end of the first conduit remote from the cuff for preventing escape of inflating fluid from the cuff.

Illustratively, the cuff comprises a sleeve including a first end, a second end, and a third region between the first and second ends. The sleeve is located around the outer cannula with at least the first end of the sleeve between the outer cannula and the third region of the sleeve.

Illustratively, the first and second ends of the sleeve are both between the outer cannula and the third region of the sleeve.

Illustratively, the apparatus further comprises a first coupler provided on an outer end of the outer cannula and a second coupler provided on an outer end of the inner cannula. Each of the first and second couplers is provided with at least one cooperating surface for guiding the inner cannula into a predetermined orientation with respect to the outer cannula when the inner cannula is inserted into the outer cannula.

Illustratively, the apparatus further comprises at least one tab provided on an outer end of one of the outer cannula and the inner cannula. The at least one tab includes an engaging surface. At least one coupler is provided on an outer end of the other one of the outer cannula and the inner cannula for engagement by the at least one tab. The at least one coupler includes a portion for cooperating with the engaging surface for orienting the inner cannula in a predetermined orientation with respect to the outer cannula.

Illustratively, the at least one tab is flexibly formed or mounted to said one of the outer cannula and the inner cannula.

According to another aspect, a tracheal tube apparatus includes a cannula having first and second ends. An inflatable cuff is formed on the cannula between the first and second ends. A conduit extends from the cuff for introducing an inflating fluid into the cuff when it is desired to inflate the cuff and removing inflating fluid from the cuff when it is desired to deflate the cuff. A gauge is coupled to the conduit for indicating the inflation pressure of the cuff.

Illustratively, the apparatus further includes a one-way valve at an end of the conduit remote from the cuff. The one-way valve prevents escape of inflating fluid from the cuff.

Illustratively, the cuff comprises a sleeve including a first end, a second end, and a third region between the first and second ends. The sleeve is located around the cannula with at least the first end of the sleeve between the cannula and the third region of the sleeve.

Illustratively, the first end of the sleeve and the second end of the sleeve are both between the cannula and the third region of the sleeve.

BRIEF DESCRIPTION OF THE DRAWINGS

The invention may best be understood by referring to the following detailed description and accompanying drawings which illustrate the invention. In the drawings.

DETAILED DESCRIPTIONS OF ILLUSTRATIVE EMBODIMENTS

Figure 1:
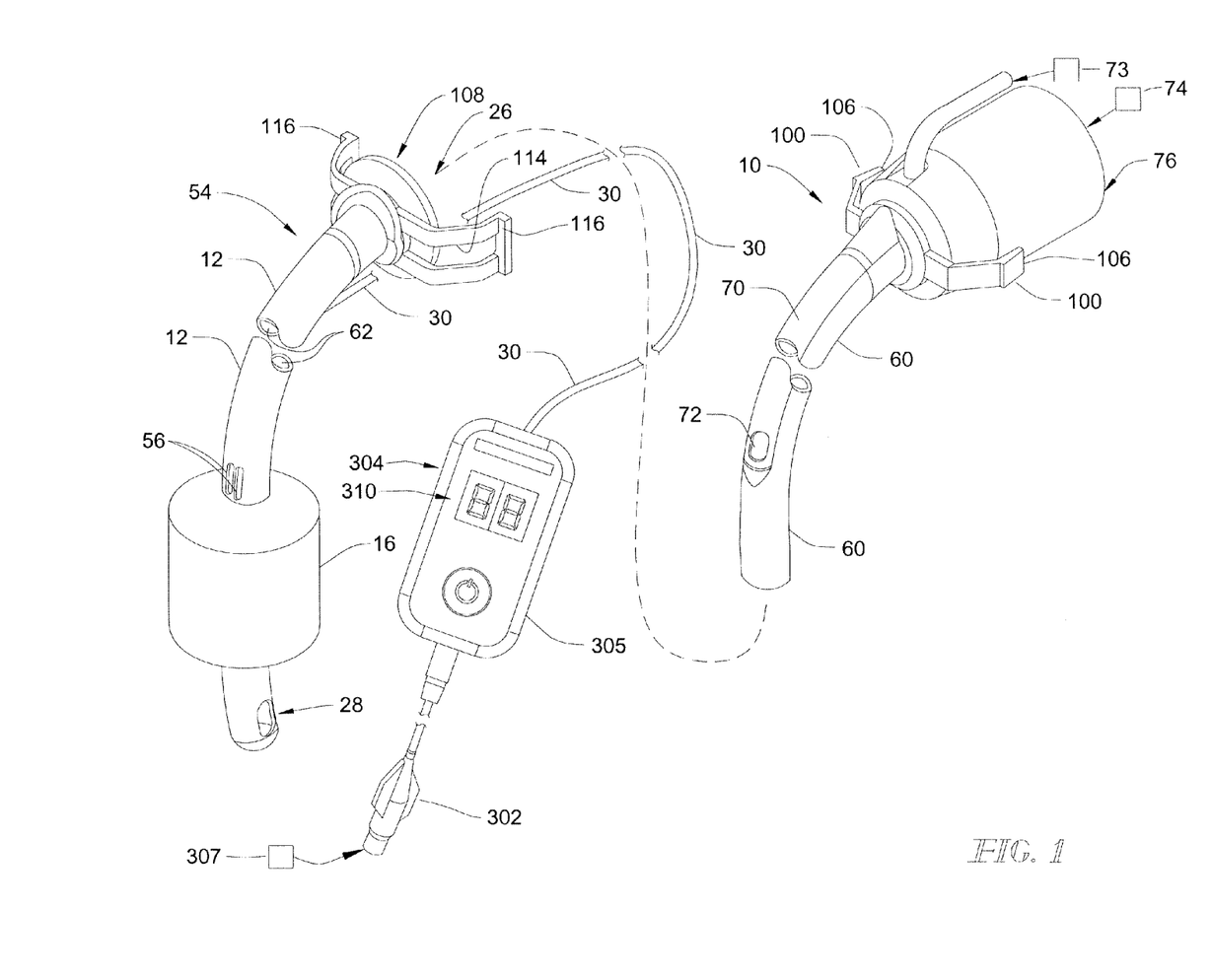
FIG. 1 illustrates a fragmentary perspective view of a system according to the invention in a disassembled configuration.
Figure 1A:
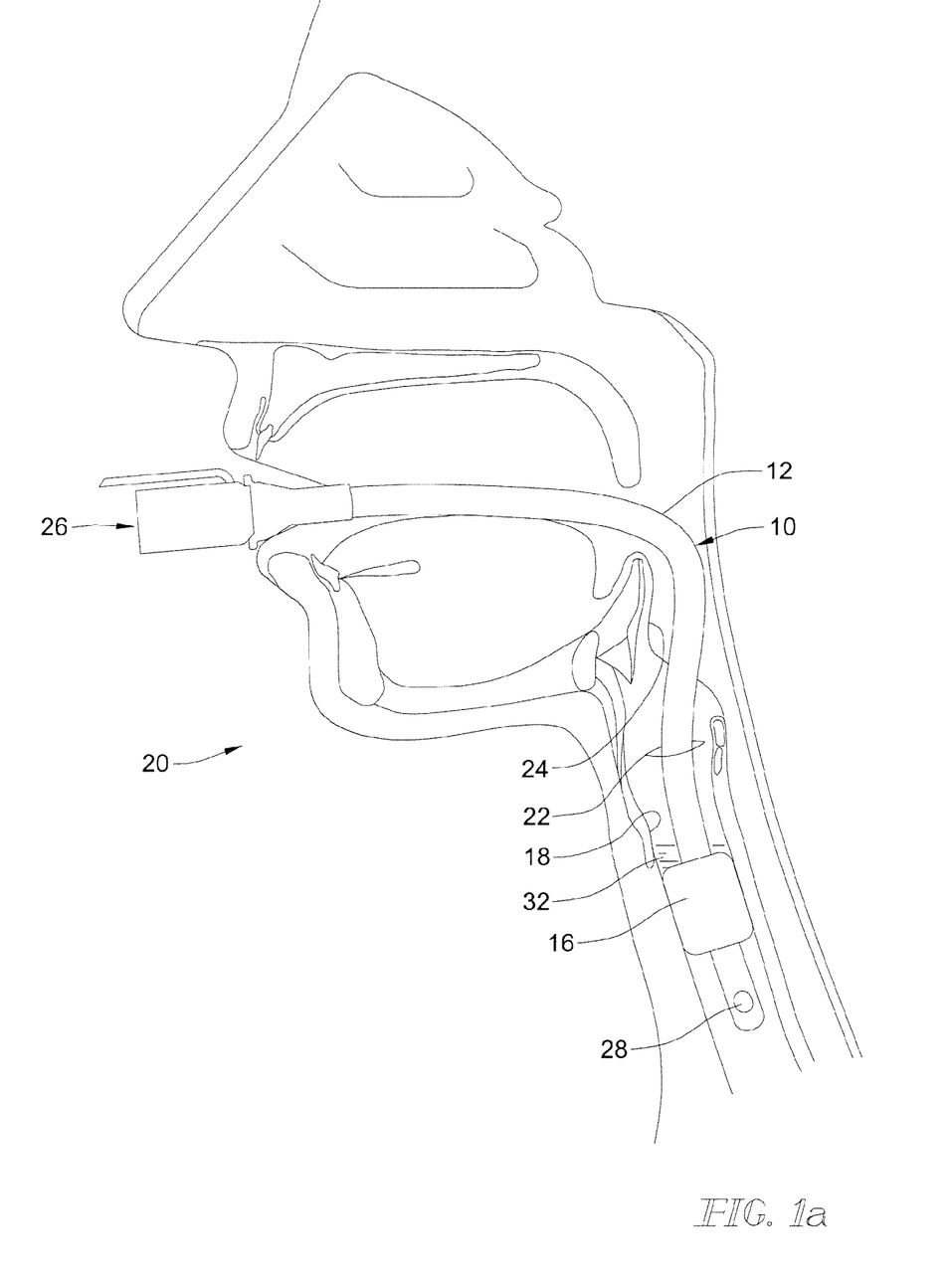
FIG. 1a illustrates a longitudinal sectional side elevational view of the anatomy of the upper airway of a wearer with the apparatus illustrated in FIG. 1 in place.
Figure 5:
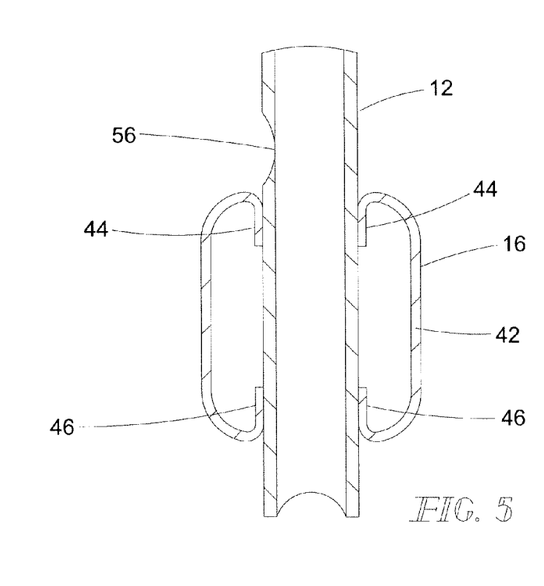
FIG. 5 illustrates an enlarged longitudinal sectional side elevational view of a detail of FIGS. 1 and 2, taken generally along section lines 5-5 of FIG. 2.
Figure 5A:
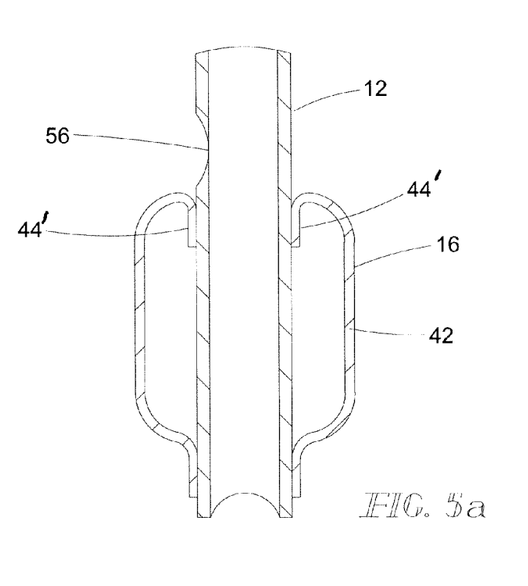
FIG. 5a illustrates an enlarged longitudinal sectional side elevational view of an alternative detail to the detail illustrated in FIG. 5.

Referring now particularly to FIGS. 1 and 1a, an endotracheal tube system 10, here an orotracheal tube system, includes an outer cannula 12 for insertion through the mouth of a wearer 20, down the wearer 20's pharynx 24, through the wearer 20's glottis 22 and into the wearer 20's trachea 18. Outer cannula 12 includes an inflatable cuff 16. Cuff 16 lies in the trachea 18 of the wearer 20 below the wearer 20's glottis 22. Outer cannula 12 also includes a first port 26 which resides outside the mouth of the wearer 20 during use and a second port 28 which resides inside the trachea 18 of the wearer 20 below cuff 16 during use. The cuff 16 is inflatable through a conduit 30 once the outer cannula 12 is in place in the trachea 18 to minimize the passage of secretions 32 from the upper respiratory tract downward into the lungs of the wearer 20. Such secretions 32 pool above the cuff 16 (that is, on the side of the cuff 16 opposite the lungs) when the cuff 16 is inflated in place. The construction of the cuff 16 as a sleeve 42, FIG. 5, with its upper and lower ends 44, 46, respectively, tucked under, rather than extending beyond the cuff 16 up and down the outer sidewall of the outer cannula 12, is aided by the use of thin-walled material for the cuff 16. In an alternative embodiment, illustrated in FIG. 5a, only upper end 44' is tucked under, rather than extending beyond the cuff 16 up the outer sidewall of the outer cannula 12'. The constructions illustrated in FIGS. 5 and 5a provide certain benefits which will be discussed subsequently.

The outer cannula 12 includes (a) fenestration(s) 56. Although two such fenestrations 56 are illustrated, it should be understood that any number of fenestrations 56 may be provided in the outer cannula 12 for this purpose. The construction of cuff 16, with its doubled-over upper and lower ends 44, 46, respectively, (FIG. 5) or doubled-over upper end 44' (FIG. 5a), permits location of the fenestration(s) 56 low (that is, more toward the lungs of the wearer 20) on the outer cannula 12. The proximity of the cuff 16 to the fenestration(s) 56 also provides some additional protection of the tissue of the trachea 18 against irritation and damage occasioned by contact with the edges of the fenestration(s) 56 by virtue of the standoff provided by the inflated cuff 16.

Figure 3:
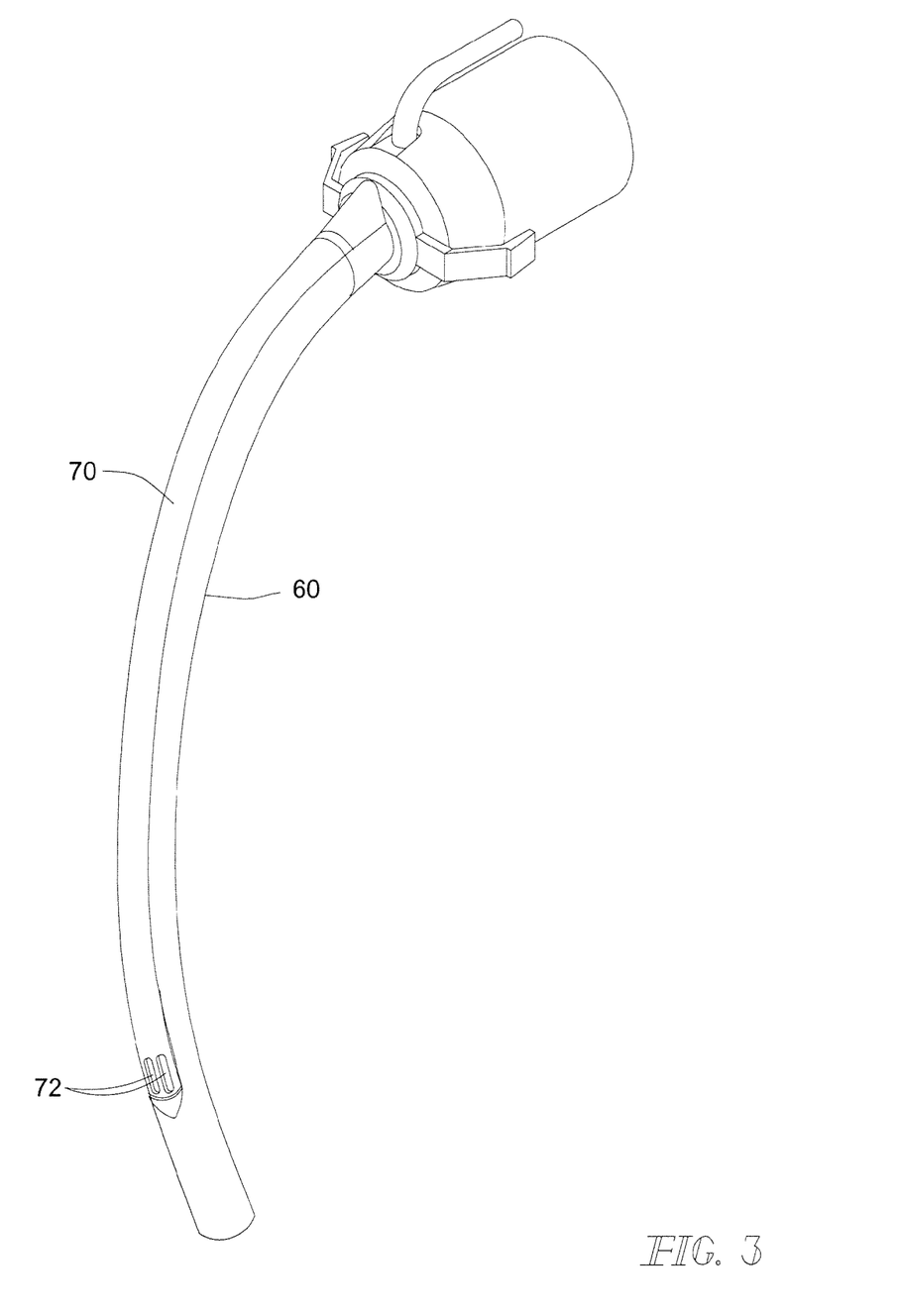
FIG. 3 illustrates a perspective view of a portion of the system illustrated in FIG. 1.
Figure 4:
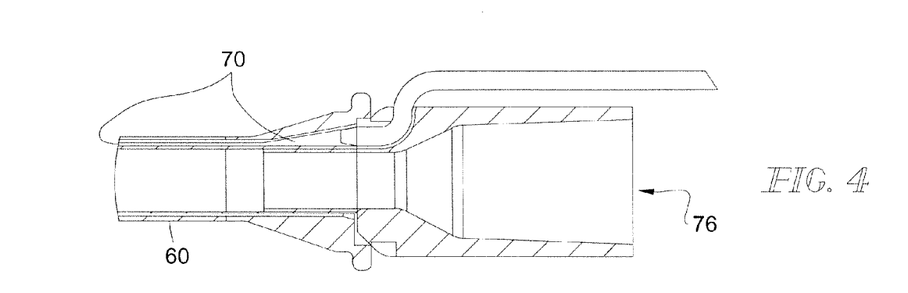
FIG. 4 illustrates an enlarged longitudinal sectional side elevational view of a detail of FIGS. 1 and 3, taken generally along section lines 4-4 of FIG. 3.

Referring now particularly to FIGS. 1 and 3, an inner cannula 60 is inserted into the lumen 62 of the outer cannula 12. To evacuate pooling secretions 32, a conduit 70 extends down the sidewall of inner cannula 60. Conduit 70 terminates at an open end 72 at the bottommost extent of fenestrations 56 to expose the secretions 32 to suction at open end 72 of tube 70 provided by a suction source 73 at the outer end of inner cannula 60. Owing to the construction of cuff 16 with its doubled-under end 44, this location generally coincides with the top of the cuff 16 at the bottommost extent of fenestration 56. Owing to this construction, extraction of secretions 32 is somewhat more predicable and complete.

In addition, it is contemplated that replacement of the inner cannula 60 may occur more frequently and with less difficulty and without much of the trauma that might attend replacement of outer cannula 12, which is typically placed in the trachea for a longer term. Typically, both the outer 12 and inner cannulae 60 are constructed from suitable filled and/or unfilled resin(s) and/or polymer(s). Inner cannula 60 typically can be relatively straightforwardly replaced by disconnecting it from the ventilator 74 (illustrated diagrammatically) to which the outer end 76 of inner cannula 60 is attached in use and withdrawing inner cannula 60 from outer cannula 12. Because of the relative ease with which inner cannula 60 can be removed, disposed of if appropriate, and replaced with a fresh cannula 60 having a fresh tube 70, providing tube 70 on inner cannula 60 rather than on outer cannula 12 affords somewhat more reliable patency of tube 70 than if the tube 70 were to be provided in outer cannula 12 which, as noted above, is typically not so readily removed for cleaning or replacement.

Referring now to FIG. 1, the inner cannula 60 is releasably fixed to an outer cannula 12 by one or more (two in the illustrated embodiment) locking tabs 100 which may be formed with, and from the same material as, the coupler 76 of cannula 60 by which cannula 60 is coupled to the ventilator 74. The tabs 100 are flexibly formed or mounted to the coupler 76 of inner cannula 60. The tabs 100 are provided with engaging surfaces 106. A coupler 108 is provided at the proximal end 54 of outer cannula 12. The coupler 108 includes a notch 114 for receiving the portion of each tab 100 which extends beyond engaging surfaces 106 and portions 116 for capturing engaging surfaces 106. This configuration also promotes correct orientation of inner cannula 60 with the fenestration(s) (56 in FIG. 1) of outer cannula 12 when inner cannula 60 is inserted into outer cannula 12.

Figure 2:
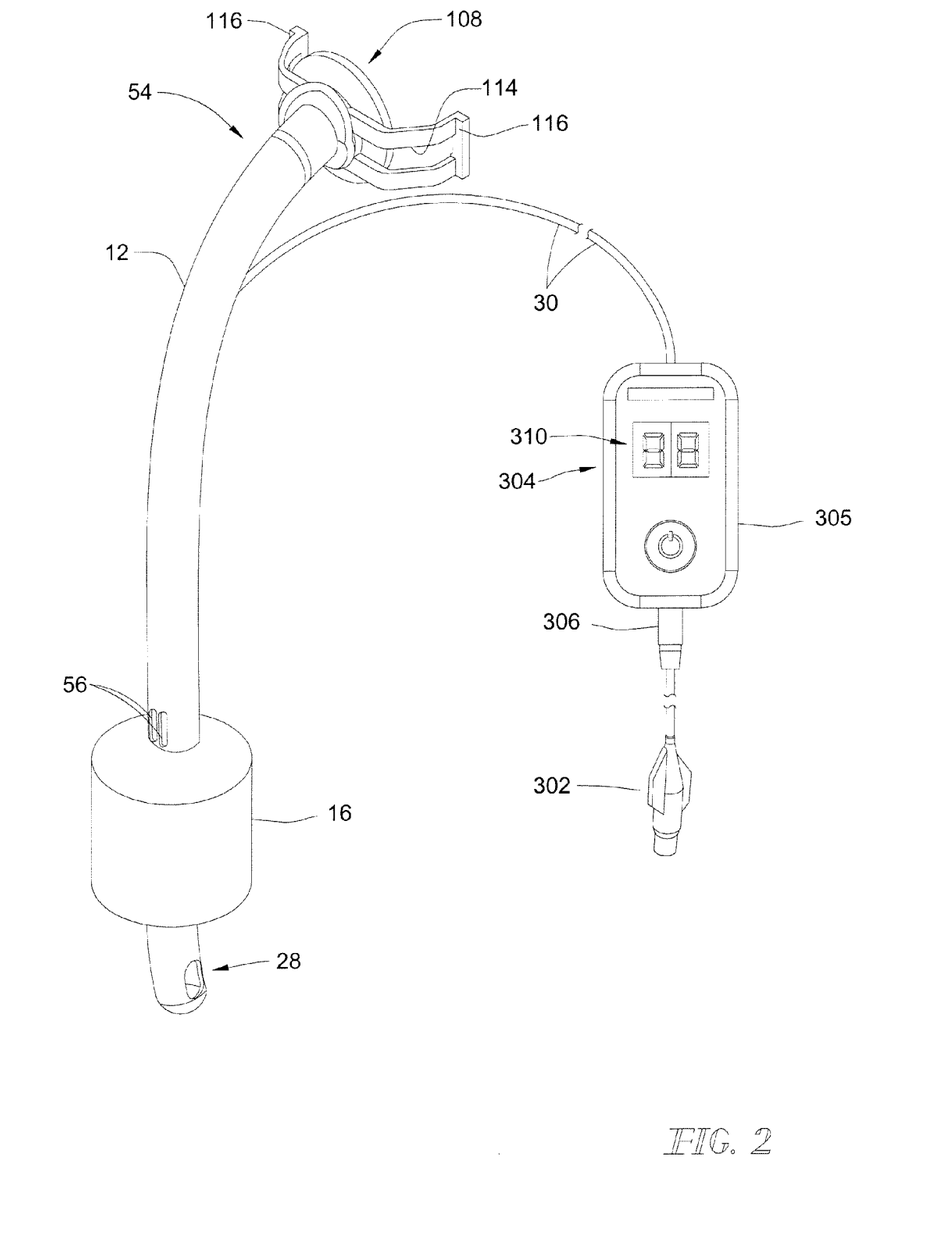
FIG. 2 illustrates a perspective view of a portion of the system illustrated in FIG. 1.

Referring to FIGS. 1 and 2, a digital pressure gauge 304 is inserted into the conduit 30 between a fitting 302 and cuff 16 by a fitting 306 provided on gauge 304. Fitting 302 is configured complementarily to a fitting on a source 307 of compressed air, such as a syringe. Such a fitting might be, for example, a Luer lock fitting or other suitable fitting to couple the compressed air source to fitting 302 for this purpose. Fitting 302 may also include a one-way valve of a suitable type, such as, for example, a ball valve, to prevent the escape of cuff 16—inflating air, permitting the compressed air source 307 to be disconnected from fitting 302 once cuff 16 is inflated to a suitable pressure.

The schematic and block circuit diagram descriptions that follow identify specific integrated circuits and other components and in many cases specific sources for these. Specific terminal and pin names and numbers are generally given in connection with these for the purposes of completeness. It is to be understood that these terminal and pin identifiers are provided for these specifically identified components. It is to be understood that this does not constitute a representation, nor should any such representation be inferred, that the specific components, component values or sources are the only components available from the same or any other sources capable of performing the necessary functions. It is further to be understood that other suitable components available from the same or different sources may not use the same terminal/ pin identifiers as those provided in this description.

Figures 6A, 6B:
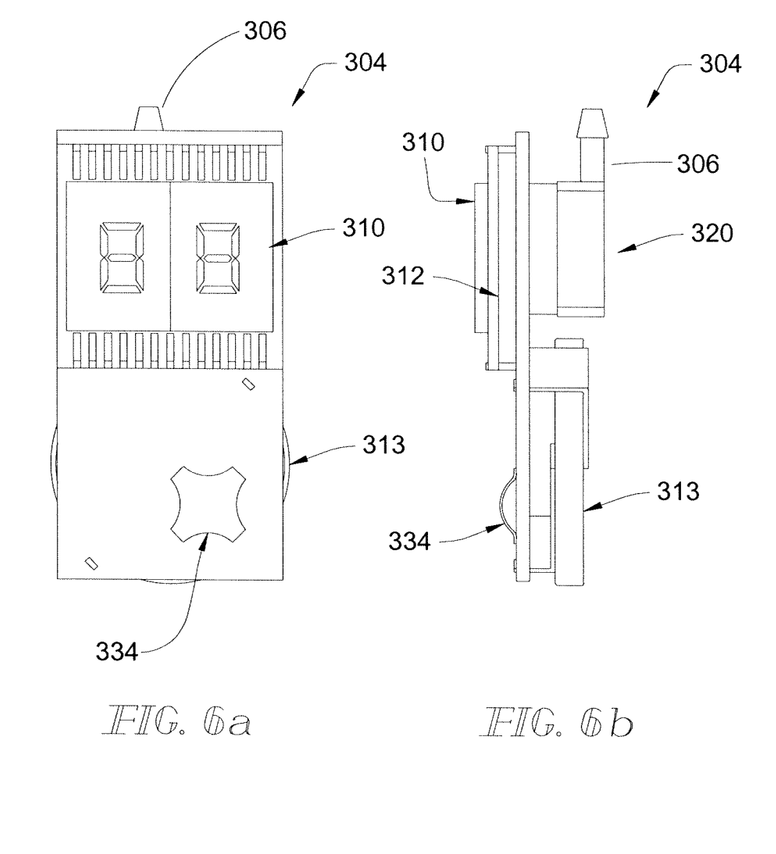
FIGS. 6a-c illustrate enlarged front elevational, side elevational and rear elevational views, respectively, of a detail of FIGS. 1 and 2; and, FIGS. 7a-e illustrate schematic circuit diagrams of the detail illustrated in FIGS. 6a-c.
Figure 6C:
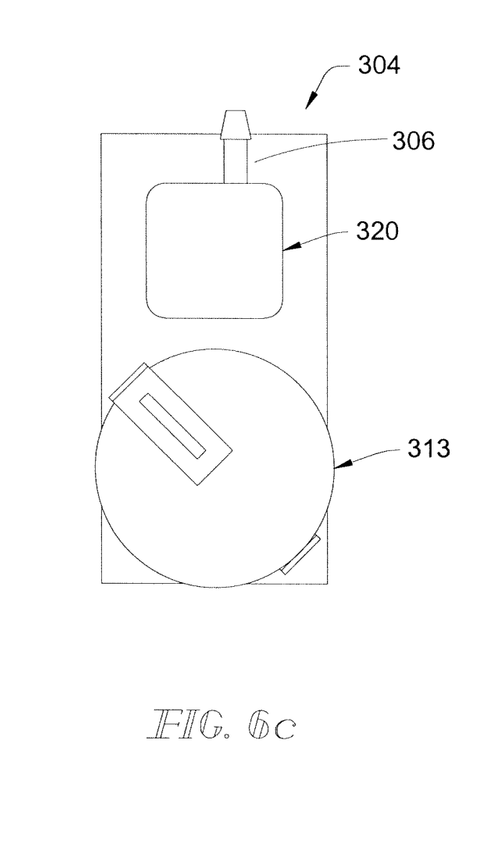
Figure 7A:
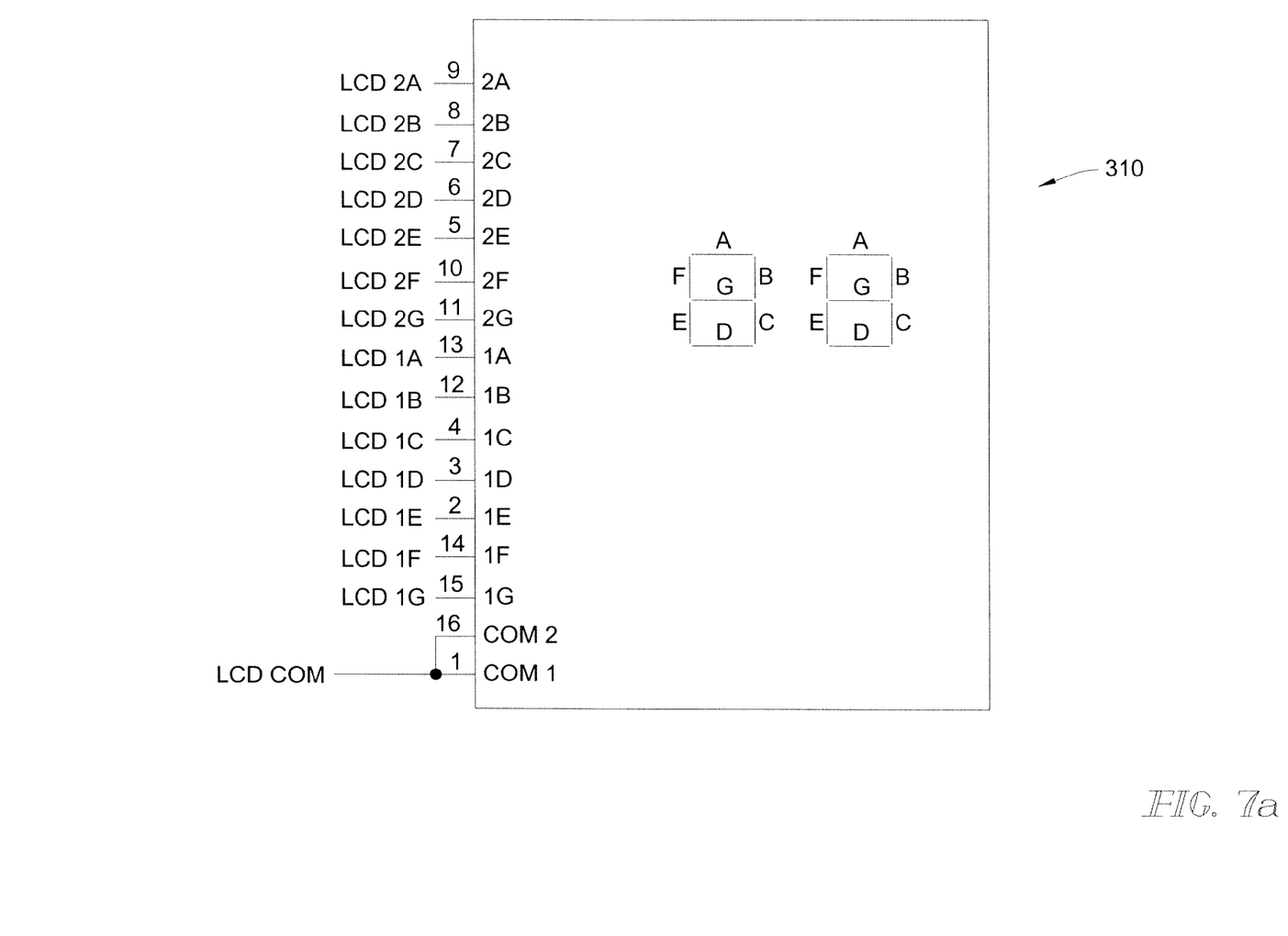
Figure 7B:
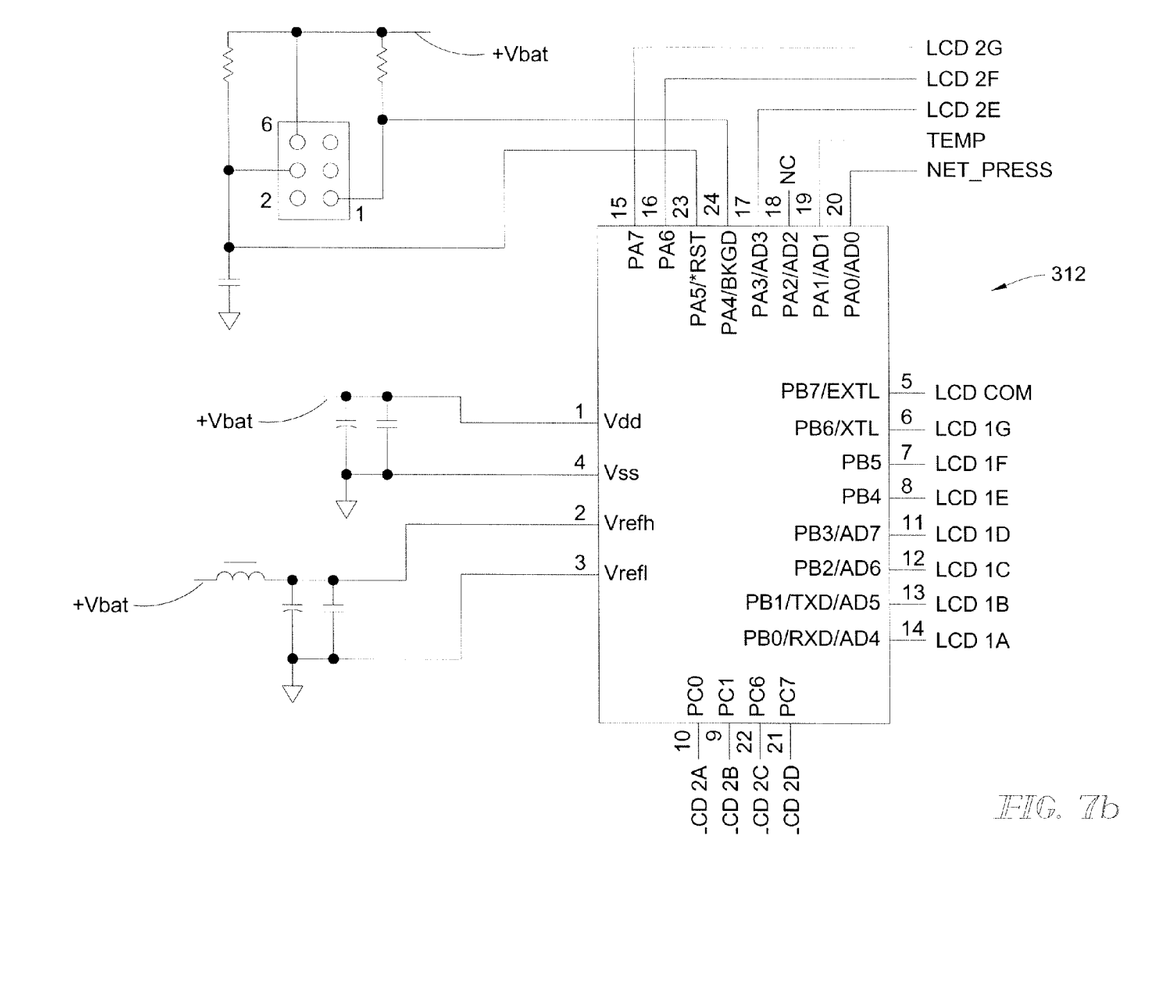

The gauge 304 removed from its housing 305 is illustrated in FIGS. 6a-c. An electrical schematic of gauge 304 is illustrated in FIGS. 7a-e. As illustrated in FIGS. 1, 2, 6a, 6b and 7a, gauge 304 includes a two digit (seven segments each) liquid crystal display (LCD) 310 which illustratively is a Glory Sound (Asia) Ltd., AE359 type DS-M2684-F display. Referring to FIGS. 6b and 7b, the driver 312 for display 310 illustratively is a Freescale Semiconductor MC9S08QB4QFN microcontroller (μC). Pins 1-4, the Vdd, Vrefh, Vrefl and Vss terminals, respectively, of driver 312 are coupled to the gauge 304's +Vbat, +Vbat, common and common terminals, respectively. Vrefh is coupled to +Vbat through a 1.8 μH inductor. +Vbat and common are the + and – terminals, respectively, of, for example, a 3V lithium PC 2 pin mount, 170 mAh coin cell 313 such as, for example, a Renata SA type 614-CR2025FH-MFR-LF coin cell. See FIGS. 6a-c.

Referring again to FIG. 7b, the parallel combination of a 2.2 μF capacitor and a 100 nF capacitor is coupled across pins 1 and 4 of μC 312. The parallel combination of a 2.2 F capacitor and a 100 nF capacitor is coupled across pins 2 and 3. Pins 5-24, terminals PB7/EXTL, PB6/XTL, PB5, PB4, PC1, PC0, PB3/AD7, PB2/AD6, PB1/TXD/AD5, PB0/RXD/AD4, PA7, PA6, PA3/AD3, PA2/AD2, PA1/AD1, PA0/AD0, PC7, PC6, PA5/*RST, and PA4/BKGD, respectively, of driver 312 are coupled to LCD COM, LCD segment 1G, LCD segment 1F, LCD segment 1E, LCD segment 2B, LCD segment 2A, LCD segment 1D, LCD segment 1C, LCD segment 1B, LCD segment 1A, LCD segment 2G, LCD segment 2F, LCD segment 2E, not connected, the gauge 304's TEMPerature terminal, the gauge 304's NET_PRESSure terminal, LCD segment 2D, LCD segment 2C, through a 100 nF capacitor to gauge 304's common terminal, and through a 4.7 KΩ resistor to +Vbat. Another 4.7 KΩ resistor is coupled between pin 23 of driver 312 and +Vbat.

Figure 7C:
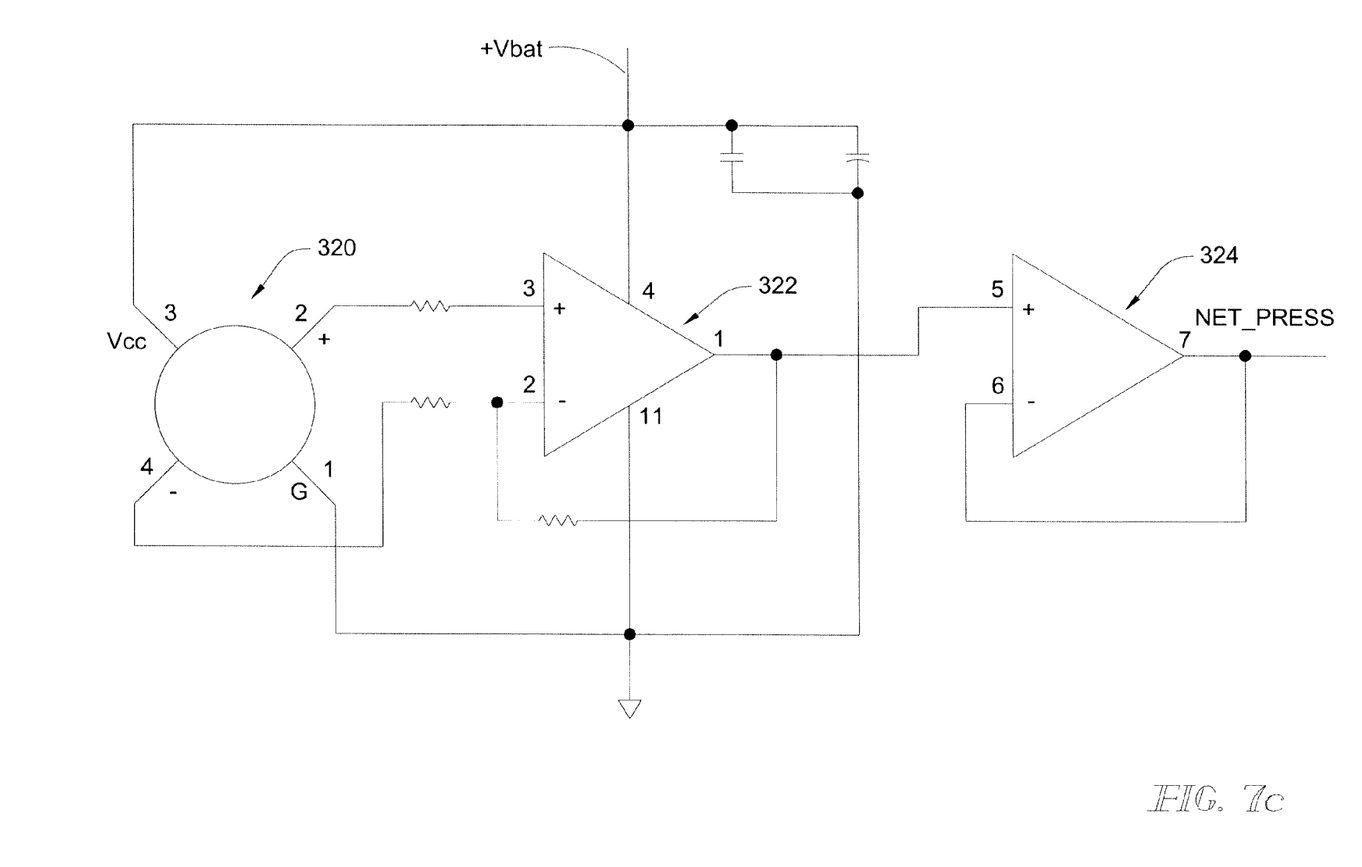

Referring to FIGS. 6b, 6c and 7c, pressure at port 306, which is the cuff 16 inflation pressure, is monitored by a pressure sensor 320, illustratively a Freescale Semiconductor type MPX10 or MPX12 uncompensated silicon pressure sensor. Sensor 320 pins 1-4 are coupled respectively to the gauge 304 common, through a 10 KΩ resistor to the non-inverting (+) input terminal, pin 3, of a differential amplifier 322, to gauge 304's +Vbat terminal, and through a 10 KΩ resistor to amplifier 322's inverting (–) input terminal, pin 2. Amplifier 322 illustratively is one-fourth of a National Semiconductor type LMC6464AIM quad differential amplifier. Feedback is provided from the output terminal, pin 1, of amplifier 322 to the – input terminal of amplifier 322 through a 100 KΩ resistor. Pin 4 of amplifier 322 is coupled to +Vbat. Pin 11 of amplifier 322 is coupled to common. The parallel combination of a 2.2 μF capacitor and a 100 nF capacitor is coupled across +Vbat and common. Pin 1 of amplifier 322 is coupled to a + terminal, pin 5 of a differential amplifier 324. An output terminal, pin 7, of amplifier 324 is coupled to amplifier 324's – input terminal, pin 6, configuring amplifier 324 as a unity gain buffer. Pin 7 of amplifier 324 forms the gauge 304's NET_PRESSure terminal. Amplifier 324 illustratively is one-fourth of a National Semiconductor type LMC6464AIM quad differential amplifier.

Figure 7D:
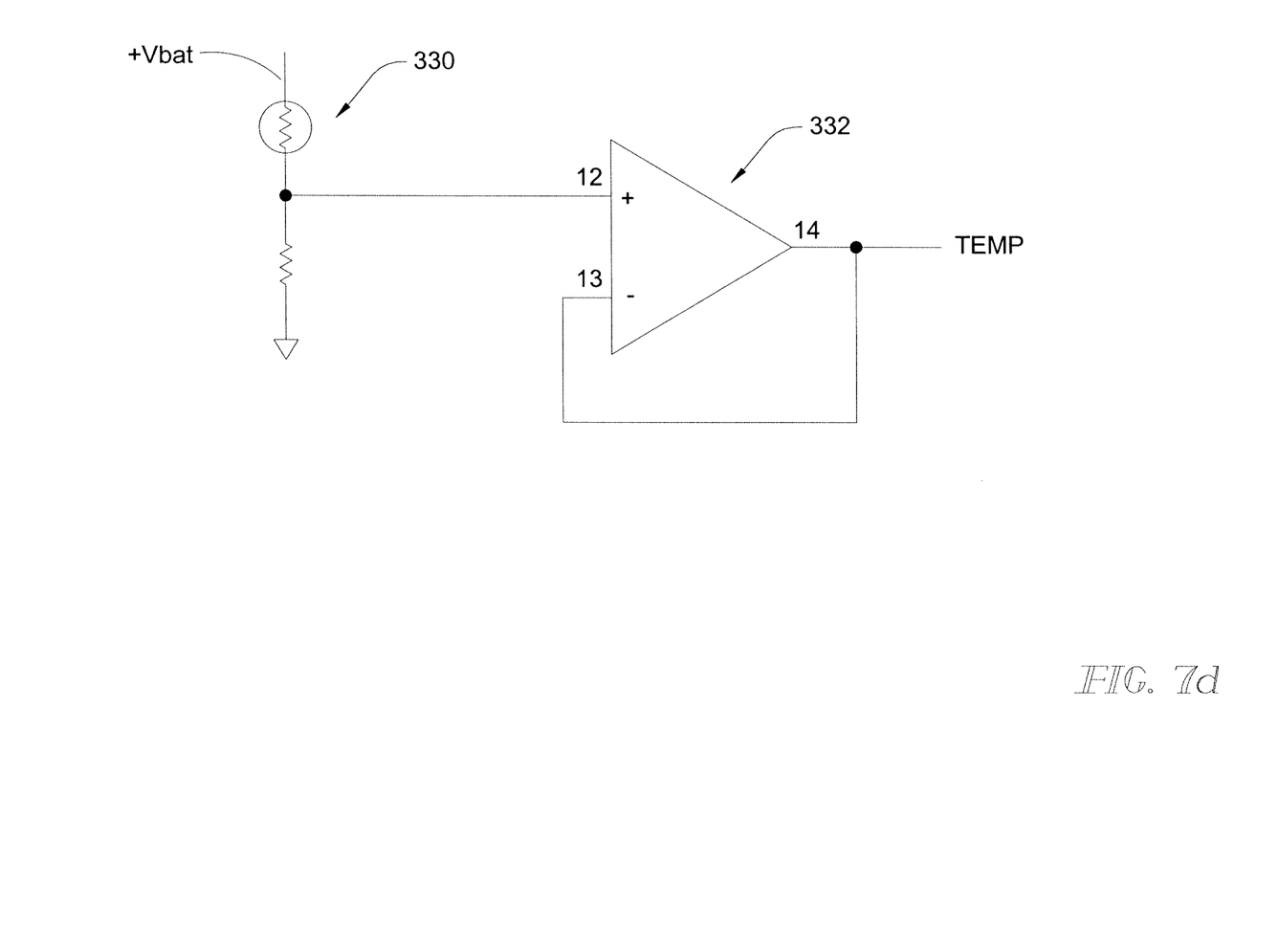
Figure 7E:
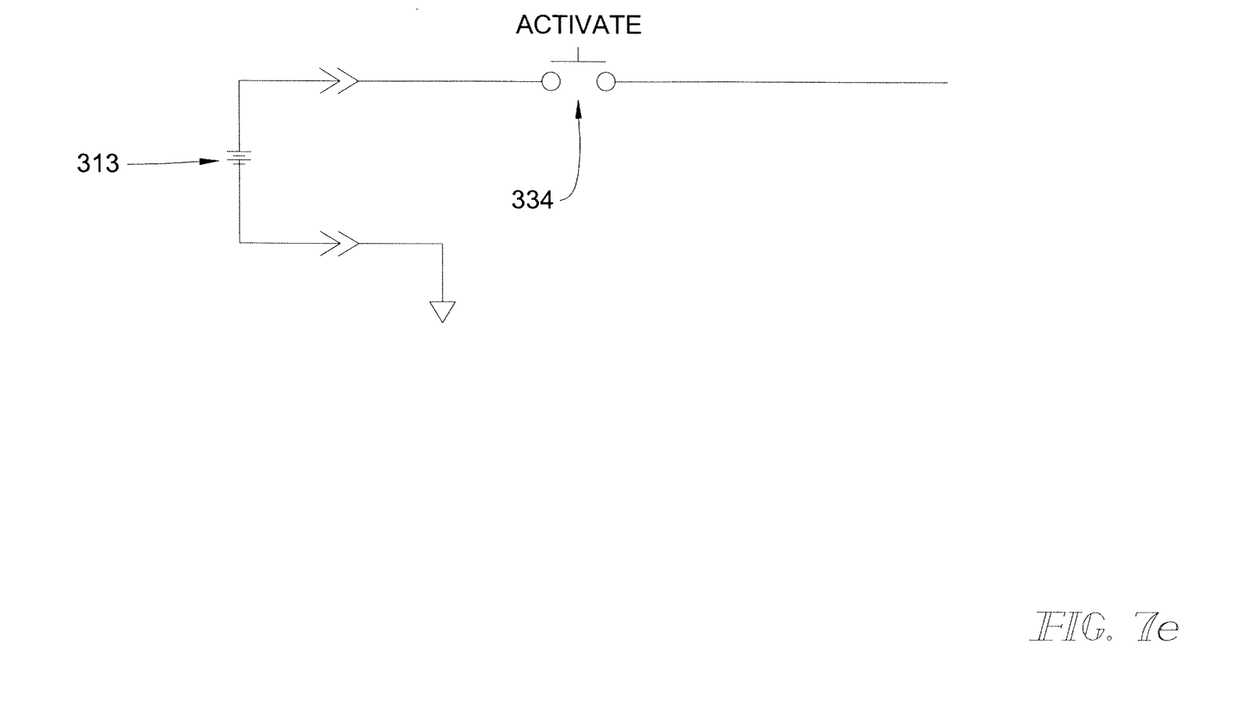

Referring to FIG. 7d, a 10 KΩ, 1% thermistor 330, such as a Vishay type 71-TFPT1206L1002FV thermistor, and a 10 KΩ, 1% resistor are coupled in series between +Vbat and common. The common terminal of thermistor 330 and the 10 KΩ resistor is coupled to the + input terminal, pin 12, of a differential amplifier 332. An output terminal, pin 14, of amplifier 332 is coupled to amplifier 332's – input terminal, pin 13, configuring amplifier 332 as a unity gain buffer. Pin 14 of amplifier 332 forms the gauge 304's TEMPerature terminal. Amplifier 332 illustratively is one-fourth of a National Semiconductor type LMC6464AIM quad differential amplifier. Referring to FIGS. 6a, 6b and 7e, +Vbat is supplied to the illustrated circuitry through a suitable switch 334, such as a Snaptron dome switch.

The topography of gauge 304 can best be understood by referring to FIGS. 6a-c, where the relative locations of fitting 306, LCD 310, driver 312, battery 313, pressure sensor 320 and switch 334 can be readily ascertained. Gauge 304 is configured to be reliable yet inexpensive in keeping with the philosophy that inner cannula 60 be rendered disposable. However, gauge 304 can be provided with a T-junction and conduit 30 and fitting 302 with appropriate complementary fittings, so that the T-junction can readily be disconnected from and reconnected into the conduit 30 between cuff 16 and fitting 302, should it be appropriate to retain the gauge 304 and dispose of the inner cannula 60. In such embodiments, gauge 304 could be reused as long as it remained operable.

What is claimed is:

1. A tracheal tube apparatus including an outer cannula having first and second ends, a fenestration along the length of the outer cannula between the first and second ends, an inflatable cuff formed on the outer cannula between the fenestration and the second end, a first conduit extending from the cuff for introducing an inflating fluid into the cuff when it is desired to inflate the cuff and removing inflating fluid from the cuff when it is desired to deflate the cuff and an inner cannula sized selectively to be inserted into, and removed from, the outer cannula, the inner cannula including first and second conduits, the second conduit to evacuate a region of a trachea of a wearer adjacent the cuff, the second conduit including an opening which lies adjacent the closest point in the fenestration to the cuff when the inner cannula is selectively inserted into a use orientation in the outer cannula.

2. The apparatus according to claim 1 further including a gauge for indicating an inflation pressure of the cuff, the gauge coupled in the first conduit.

3. The apparatus according to claim 2 further including a one-way valve at an end of the first conduit remote from the cuff, the one-way valve preventing escape of inflating fluid from the cuff.

4. The apparatus according to claim 1 further including a one-way valve at an end of the first conduit remote from the cuff, the one-way valve preventing escape of inflating fluid from the cuff.

5. The apparatus according to claim 1 wherein the cuff comprises a sleeve including a first end, a second end, and a third region between the first and second ends, the sleeve located around the outer cannula with at least the first end of the sleeve between the outer cannula and the third region of the sleeve.

6. The apparatus according to claim 5 wherein the first end of the sleeve and the second end of the sleeve are both between the outer cannula and the third region of the sleeve.

7. The apparatus according to claim 2 wherein the cuff comprises a sleeve including a first end, a second end, and a third region between the first and second ends, the sleeve located around the outer cannula with at least the first end of the sleeve between the outer cannula and the third region of the sleeve.

8. The apparatus according to claim 7 wherein the first end of the sleeve and the second end of the sleeve are both between the outer cannula and the third region of the sleeve.

9. The apparatus according to claim 4 wherein the cuff comprises a sleeve including a first end, a second end, and a third region between the first and second ends, the sleeve located around the outer cannula with at least the first end of the sleeve between the outer cannula and the third region of the sleeve.

10. The apparatus according to claim 9 wherein the first end of the sleeve and the second end of the sleeve are both between the outer cannula and the third region of the sleeve.

11. The apparatus according to claim 1 further comprising a first coupler provided on an outer end of the outer cannula, a second coupler provided on an outer end of the inner cannula, one of the first and second couplers provided with at least one surface for guiding the inner cannula into the use orientation with respect to the outer cannula when the inner cannula is inserted into the outer cannula, the other of the first and second couplers provided with a cooperating surface for cooperating with the at least one surface for guiding the inner cannula into the use orientation with respect to the outer cannula.

12. The apparatus according to claim 2 further comprising a first coupler provided on an outer end of the outer cannula, a second coupler provided on an outer end of the inner cannula, one of the first and second couplers provided with at least one surface for guiding the inner cannula into the use orientation with respect to the outer cannula when the inner cannula is inserted into the outer cannula, the other of the first and second couplers provided with a cooperating surface for cooperating with the at least one surface for guiding the inner cannula into the use orientation with respect to the outer cannula.

13. The apparatus according to claim 4 further comprising a first coupler provided on an outer end of the outer cannula, a second coupler provided on an outer end of the inner cannula, one of the first and second couplers provided with at least one surface for guiding the inner cannula into the use orientation with respect to the outer cannula when the inner cannula is inserted into the outer cannula, the other of the first and second couplers provided with a cooperating surface for cooperating with the at least one surface for guiding the inner cannula into the use orientation with respect to the outer cannula.

14. The apparatus according to claim 1 further comprising at least one tab provided on an outer end of one of the outer cannula and the inner cannula, the at least one tab including an engaging surface, at least one coupler provided on an outer end of the other one of the outer cannula and the inner cannula for engagement by the at least one tab, the at least one coupler including a portion for cooperating with the engaging surface for orienting the inner cannula in the use orientation with respect to the outer cannula.

15. The apparatus according to claim 14 wherein the at least one tab is flexibly formed or mounted to said one of the outer cannula and the inner cannula.

16. The apparatus according to claim 2 further comprising at least one tab provided on an outer end of one of the outer cannula and the inner cannula, the at least one tab including an engaging surface, at least one coupler provided on an outer end of the other one of the outer cannula and the inner cannula for engagement by the at least one tab, the at least one coupler including a portion for cooperating with the engaging surface for orienting the inner cannula in the use orientation with respect to the outer cannula.

17. The apparatus according to claim 16 wherein the at least one tab is flexibly formed or mounted to said one of the outer cannula and the inner cannula.

* * * * *